United States Patent [19]

Baumoel

[11] 4,373,401
[45] Feb. 15, 1983

[54] TRANSDUCER STRUCTURE AND MOUNTING ARRANGEMENT FOR TRANSDUCER STRUCTURE FOR CLAMP-ON ULTRASONIC FLOWMETERS

[76] Inventor: Joseph Baumoel, 107 Columbia Dr., Jericho, Long Island, N.Y. 11753

[21] Appl. No.: 146,530

[22] Filed: May 5, 1980

[51] Int. Cl.³ ............... G01F 1/66; G01N 29/02
[52] U.S. Cl. .................. 73/861.18; 73/644; 310/327; 310/334
[58] Field of Search ........... 73/861.25, 861.26, 861.27, 73/861.28, 597, 632, 644, 598, 861.18; 310/327, 334, 335, 336

[56] References Cited

U.S. PATENT DOCUMENTS

| | | | |
|---|---|---|---|
| 2,525,861 | 10/1950 | Carlin | 73/644 |
| 2,912,854 | 11/1959 | Schubring | 73/644 |
| 3,074,268 | 1/1963 | Rafferty et al. | 73/644 |
| 3,237,453 | 3/1966 | Yamamoto et al. | 73/861.28 |
| 3,279,242 | 10/1966 | Megoloff | 73/644 |
| 3,427,481 | 2/1969 | Lenahan et al. | 310/327 |
| 3,546,924 | 12/1970 | Nussbaum et al. | 73/644 |
| 3,575,050 | 4/1971 | Lynnworth | 73/861.27 |
| 3,661,146 | 5/1972 | Peronneau et al. | 310/327 X |
| 3,987,674 | 10/1976 | Baumoel | 73/861.28 |

FOREIGN PATENT DOCUMENTS

148946  7/1962  U.S.S.R. .................. 310/327

*Primary Examiner*—Charles A. Ruehl
*Attorney, Agent, or Firm*—Ostrolenk, Faber, Gerb & Soffen

[57] ABSTRACT

A transducer crystal is coupled to a coupling plastic material made of a compression molded polyimid amide. Two cooperating transducer housings are formed of two wedges of material cut from the same rectangular billet. The wedge angle is calculated after measuring the sonic velocity of the billet. A novel buffer is applied to the rear surface of the transducer crystal and consists of an epoxy body having tungsten powder and small particles of an elastomer distributed therein. The transducer body is mounted on a support track which has a similar configuration for numerous different mounting arrangements. The transducer housings are axially spaced from one another along the axis of the pipe and are set to a given spacing by locating a mounting clip on an index plate on the track. Transducers for a portable type application have tracks connected to one another along one of their sides by a flexible but tough sheet of material which fixes the spacing of the tracks for a given pipe diameter. The opposite rails of the two tracks are connected together by a quick release strap arrangement.

9 Claims, 28 Drawing Figures

TRANSDUCER STRUCTURE AND MOUNTING ARRANGEMENT FOR TRANSDUCER STRUCTURE FOR CLAMP-ON ULTRASONIC FLOWMETERS

BACKGROUND OF THE INVENTION

This invention relates to a novel transducer housing and mounting arrangement therefor for a transducer which is particularly applicable for use with a clamp-on type of ultrasonic flowmeter.

Clamp-on type ultrasonic flowmeters are shown in U.S. Pat. No. 3,987,674. A clamp-on assembly for an ultrasonic liquid level sensor is shown in copending application Ser. No. 6,183, filed Jan. 24, 1979 (now U.S. Pat. No. 4,203,324), entitled Sonic Liquid Level Detector in the name of Baumoel.

In tranducers of this type, it is desirable to couple sonic energy into a fluid carrying pipe in the most efficient noise-free manner possible. It is also very desirable that the transducer housings can be easily sonically coupled to the pipe in order to carry out their function.

Transducers used in the past have been effective in use but limited in their application and performance. Moreover, the transducers used in the past could not be used over wide temperature ranges and did not produce the optimum noise-free operation. Finally, the prior mounting for the transducer housings was expensive and complex, and less precise than the structure described herein.

BRIEF DESCRIPTION OF THE INVENTION

In accordance with the present invention, a novel transducer structure is provided along with novel mounting means for mounting the transducer to a pipe or conduit.

The novel transducer housing of the invention contains numerous features including a novel coupling material for coupling the transducer crystal to the pipe wall; a novel sonic damping arrangement; and a novel mounting structure permitting the mounting of the transducer housing.

The coupling plastic material of the invention approaches, more so than most plastics, the temperature characteristics of steel and is very stable over a wide temperature range with respect to its sonic characteristics. The material discovered for this purpose is a polyimid amide known by the trademark Meldin 470.

This material may be used as the entire housing body or, to reduce costs, it may be formed in the shape of a right angle wedge extending from the front face of the piezoelectric transducer crystal to the bottom surface of the transducer housing which is coupled to the pipe along the hypotenuse of the wedge. When used for a flowmeter, as shown in U.S. Pat. No. 3,987,674, two transducer assemblies are required on opposite sides of a pipe. The wedge angle must be related to the particular materials used such that $$\sin \alpha = V_c/V_{pc},$$

where $\alpha$ is the angle between the front transducer crystal face and the axis of the pipe to which the crystal is connected;

$V_c$ is the velocity of sound in the coupling wedge;

and $V_{pc}$ is the group velocity of sound in the pipe wall material.

To ensure this condition, the two transducer coupling wedges are made of the same rectangular billet, and the billet is cut to produce the two wedges only after the sonic velocity of the billet has been measured. The wedge shape is then appropriately trimmed to produce the optimum angle for the particular pipe material to which the transducers are to be connected. Note that only a relatively small number of different pipe materials are in common use for carrying fluids so that only a small number of wedge angles will be necessary in the transducer housing.

The piezoelectric transducer crystal has a rear surface, the energy of which must be absorbed to prevent the energy emitted at the rear surface from interferring with the energy transmitted to the pipe and fluid being monitored.

A novel damper is provided to the crystal back surface. The damper consists of a mass of material having a sonic impedance close to that to the impedance of the crystal to ensure that the sonic energy will enter the damper. The damper, however, consists of a plastic mass having suspended in it heavy metal particles such as those of tungsten, and an absortive filler of some desired elastomer such as a polysulphone which may be the polysulphone sold under the trademarks Hytrel. The particle size of the metal and of the elastomer is preferably related to the wavelength of the sonic energy entering the buffer in order to most effectively, disturb the coherency of the sonic energy entering the buffer. Moreover, the rear surface of the buffer has an inwardly projecting conical surface or related shape to increase path length and angle of incidence of the sonic energy passing through the buffer and reflecting back from its rear surface.

The main body of the damper can be any suitable epoxy or the like. Note that the tungsten powder distributed throughout the body and the absorptive elastomer filler distributed throughout the epoxy body can be of any material which will scatter and absorb the sonic energy in the desired manner.

The transducer housings are then provided with mounting ears on the opposite ends of the transducer body. These mounting ears are used to mount the transducer housing in novel support tracks which can be easily strapped or otherwise secured to the outer surface of the conduit which is to receive the transducers. Each of the track assemblies consists of spaced tracks or rails which are fixed to one another at a fixed spacing. The spaced tracks then have sliding mounting clips captured thereon. The transducer housing is then placed between two mounting clips, and its mounting ears are fixed to the clips as by screws which pass through the ears and threaded into threaded openings in the mounting clips. The mounting ears on the transducer bodies are at a height on the transducer body to ensure that the bottom surface of the transducer housing containing the end of the coupling wedge or its equivalent can be pressed tightly against the pipe when the mounting tracks are strapped to the pipe.

The mounting tracks and their respective transducer housings are then clamped to opposite surfaces of the pipe by suitable flexible straps which fix the transducer housings at a given axial distance apart. In some cases where the transducer housing is to be easily removable from a conduit as in a portable measurement apparatus, the opposite track assemblies can be fixed to one another along one of their sides by a flexible but tough sheet which has a dimension which will fix the tracks in parallel relationship with one another on opposite sides of the pipe of a given diameter. The other sides of the two tracks can then be secured by suitable clampable straps. The assembly can then be easily and conveniently connected to pipes of given diameter at any location in a system.

The tracks used in the mounting arrangement of the present invention are provided with indexing strips so that the transducer housings can be mounted at a given index location having an identifiable numeral which will identify the axial spacing of the two transducers mounted on opposite sides of a pipe. This known axial index can then be used as an input to the measurement circuitry of a flowmeter so that the circuitry will have data regarding the spacing of the transducers. In this way, the circuitry can be automatically compensated during its operation when different fluids having different sonic velocities are introduced into the conduit receiving the transducers. That is to say, as described in copending application Ser. No. 6, 183 (now U.S. Pat. No. 4,203,324), the axial spacing the transducers is functionally related to the sonic velocity in the fluid being measured. By providing an input to the circuitry of the fixed spacing of the transducers, other compensations can be made in the measurement circuit to compensate for a change in fluid being carried by the conduit under consideration.

It should be noted that while the transducer structure of this invention is intended for use in an ultrasonic flowmeter application, the transducer concepts have application to transducer structures for any application.

DETAILED DESCRIPTION OF THE DRAWINGS

Referring first to FIGS. 1 through 7, there is illustrated therein a transducer structure which has particular applicability to the transducer of an ultrasonic flowmeter of the type shown in U.S. Pat. No. 3,987,674 and in pending application Ser. No. 6,183 (now U.S. Pat. No. 4,203,324). It will, however, be recognized that the concepts used in the novel transducer may be carried over to other transducer configurations in virtually any transducer application.

The main transducer crystal of the assembly is the transducer crystal 30 (FIGS. 2 and 6) which can, for example, be a lead zirconium titanate type transducer element which is a circular disk having a thickness and diameter as required in a particular application. The outer face of the crystal 30 forms a critical angle $\alpha$ with the bottom of the housing in FIG. 2 and the angle $\alpha$ will be the arc sine of the product of the velocity of sound in the coupling material to the group velocity in the material to which the transducer is coupled. This angle is preferably fixed for each transducer assembly so that it will be matched to the particular pipe material with which the transducer is associated. In normal commercial applications, only a relatively few different type materials will be encountered so that the angle will have only a few discrete approximate values.

Figure 5:
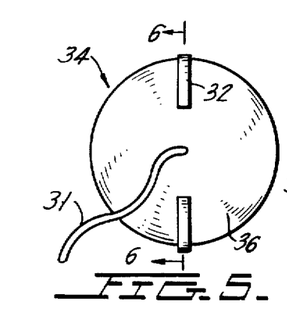
FIG. 5 is a top view of the transducer damper of the invention.
Figure 6:
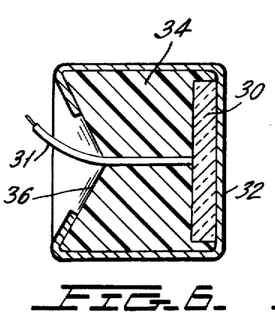
FIG. 6 is a cross-sectional view of FIG. 5 taken across the section line 6—6 in FIG. 5.
Figure 7:
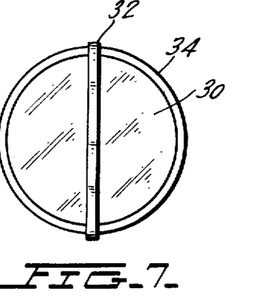
FIG. 7 is a bottom view of FIGS. 5 and 6.

Transducer crystal 30 has a rear electrode to which conductor 31 is soldered and will also have a front electrode foil strip 32 best shown in FIGS. 5, 6 and 7. By applying a suitable potential between conductors 31 and 32, a suitable mechanical oscillation of the crystal 32 will be excited.

Crystal disk 32 is mounted within a novel damper assembly comprised of damper disk 34 best shown in FIGS. 2, 5, 6 and 7. Damper 34 has the purpose of absorbing the production of the rearward ultrasonic wave in response to excitation of the crystal 30.

In accordance with the present invention, a sonic wave from the crystal 30 can easily enter the damper 34 but, once in the damper material, the wave is trapped and damped and prevented from leaving the damper. In particular, damper 34 is made of a novel composition consisting of a suitable plastic body which contains a metal powder and an absorptive filler of an elastomer having a particle size related to the wavelength of the sonic energy which enters the body 34.

In a preferred embodiment of the invention, the plastic material of member 34 can be any suitable epoxy or other bulk material having accoustic impedance matched to those of the crystal 30, loaded with a heavy metal powder (such as tungsten powder) and also loaded with an absorptive filler material of Hytrel, a polysulphone or other elastomeric material, which has a particle size related generally to the wavelength of the ultrasonic energy which enters the body 34. It has been found that the use of this combination permits sonic energy to enter the body 34 but, once the sonic energy enters the body 34, it is trapped therein and will not leave the body. More particularly, the energy tends to interact with the elastomer particles and the tungsten particles and the sonic waves are scattered and made incoherent. Thus, all coherent sonic energy entering the body 34 is substantially attenuated, and energy which escapes from the body will not leave the body in a coherent form and cannot interfere with subsequent measurements relying on the coherency of the sonic beams produced by the crystal 30.

To further improve the operation of the damper, a conical depression 36 is formed in the damper (FIGS. 2, 5 and 6) where the conical depression 36 increases the sonic path length from the crystal 30 and varies the angle of incidence on the internal surface of surface 36.

The transducer crystal 30 and its damper 34 are suitably fixed together and are then loaded into a circular opening 37 in the rectangular coupling body 38 which forms the transducer housing. A securing strap 39 (FIGS. 2 and 4) is placed over the damper 34 and holds the damper and crystal assembly firmly in place within opening 37. Note that the plate 39 is screwed to the body 38 as by the screws 40 and 41 in FIGS. 2 and 4.

Figures 1, 4:
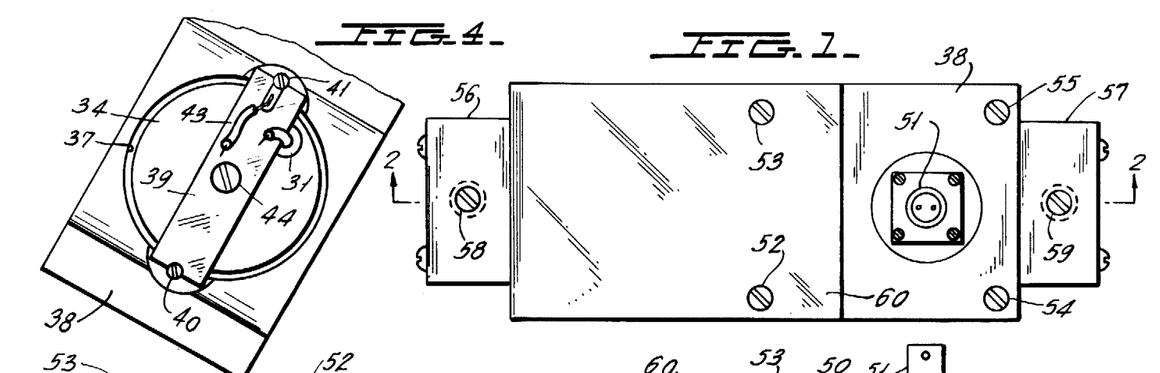
FIG. 1 is a plan view of a first embodiment of a transducer structure of the invention.
FIG. 4 is a view of FIG. 2 taken across the section line 4—4 with the angle plate removed to permit viewing of the transducer elements.
Figure 2:
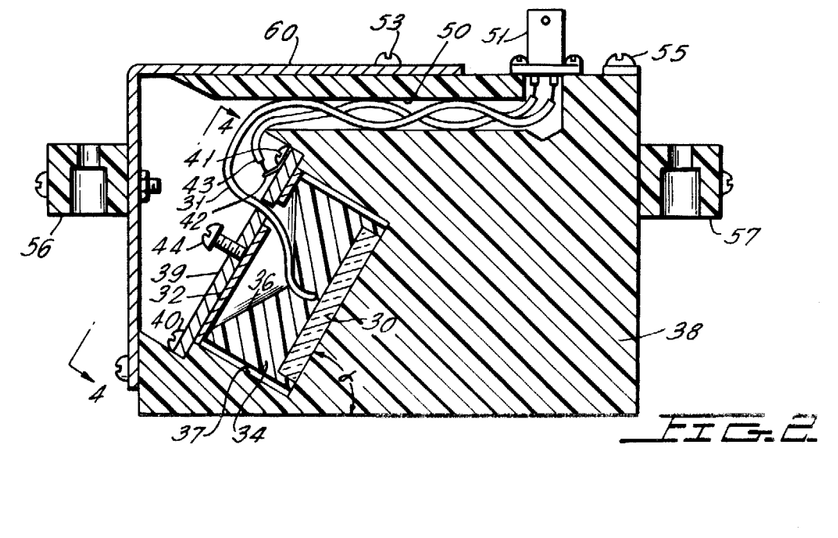
FIG. 2 is a cross-sectional of FIG. 1 taken across the section line 2—2 in FIG. 1.
Figure 3:
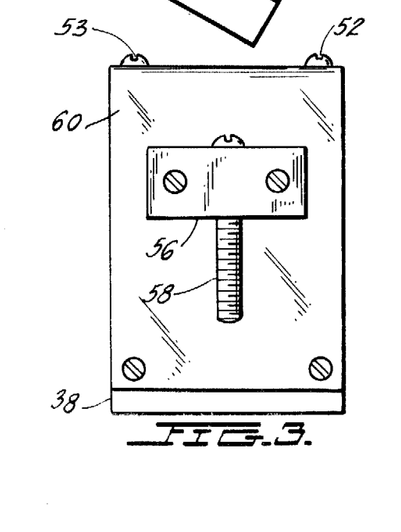
FIG. 3 is an elevation view of FIG. 2.

The electrode 32, which is the front electrode of crystal 30, is electrically connected to the plate 39 and a terminal 42 for the front electrode is arranged with the screw 41 as shown in FIG. 2. A conductive wire 43 is connected to terminal 42. A pressure screw 44 is connected to the plate 39. The wires 43 and 31 are then carried through a channel 50 which is machined in the body 38 and are connected to a suitable conventional connector 51. A suitable NEMA approved housing or portable type connector can then be fixed atop connector 51 at the screws 52, 53, 54 and 55 (FIG. 1).

Mounting lugs 56 and 57 for mounting the transducer housing have captured screws 58 and 59, respectively, (FIGS. 1 and 3) and are fixed to the metal angle plate 60 and the body 38, respectively. The angle plate 60 covers the end of opening 37 which receives the transducer crystal assembly.

A significant aspect of the invention lies in the materials selected for the body 38. More specifically, body 38 is selected to be a high temperature plastic which will be very stable with temperature. That is to say, since the transducer will be coupled to pipe which may carry very hot fluid, the plastic material must withstand very high temperature and the variation of acoustic velocity in the body 38 at different temperatures must be limited. A very superior material for this purpose has been found to be a polyimid amide which has been compression-molded. One satisfactory polyimid amide is material sold under the trademark Meldin 470, which exhibits the desired characteristics and is very useful in connection with steel pipe. Steel is frequently the material used for the pipe to which the body 38 is coupled. Thus, the use of the polyimid amide will give good transducer operation over a wide range of temperature for many pipes which require flow rate monitoring.

Extremely good results are obtained with the transducer housing disclosed in FIGS. 1 through 7. However, the preferred material for body 38 is relatively expensive and, when the transducer body must be fairly large, it is preferably that the entire body not be made of the polyimid amide plastic while it is still desirable to retain the coupling characteristics of the plastic. Thus, for relatively large transducers, a wedge of the Meldin polyimide amide has been used, with the remaining body of the transducer filled with some less expensive plastic material. An arrangement of this kind is shown in FIGS. 11 through 17.

Referring to FIGS. 10 to 13, there is shown a rectangular wedge 60 of a compression molded polyimid amide which has two mounting flanges 61 and 62 which receive bolts such as the bolts 63, 64 and 65 which fix the wedge-shaped body 60 to the rectangular metal container 66. Contained within the metal can 66 is an assembly of transducer crystal 30 and damper 34 which is identical to that described in connection with FIGS. 1 to 7. A rectangular cover plate 67 is then connected over the end of container 66 and is connected thereto by screws such as screws 68 and 69 in FIG. 11.

A circular pressure plate 70 (FIG. 13) having an opening 71 therein is then placed atop the damper 34 and the pressure screw 73 is tightened to force the pressure plate 70 into contact with the damper 34 and, at the same time, makes electrical connection to the front contact foil of the transducer crystal 31. An electrical terminal 75, associated with screw 78, permits electrical connection to the transducer crystal front contact. The rear contact wire 38 of the transducer crystal 30 is threaded through the opening 71 in plate 70 and is connected to the terminal connector 76 on plate 67.

Figure 8:
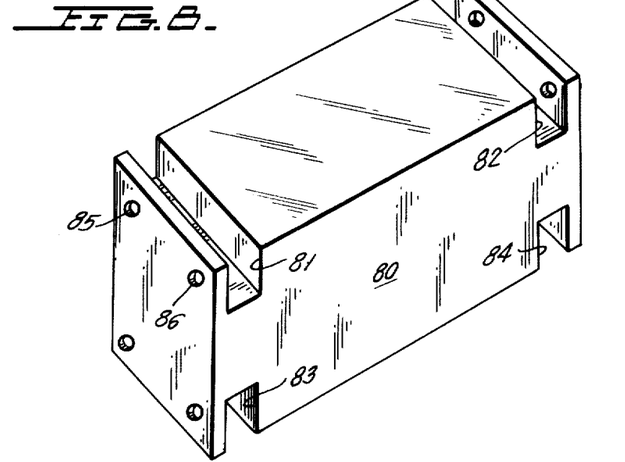
FIG. 8 is a perspective view of a billet of ultrasonic coupling material which is to be processed to make an ultrasonic energy coupling wedge.
Figure 9:
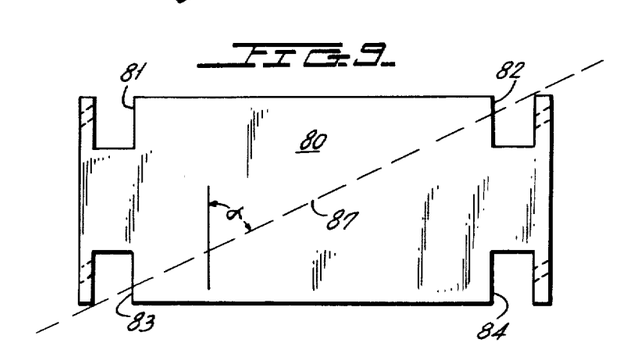
FIG. 9 is a side view of the billet of FIG. 8 prior to slicing the billet to wedge-shaped sections.
Figure 10:
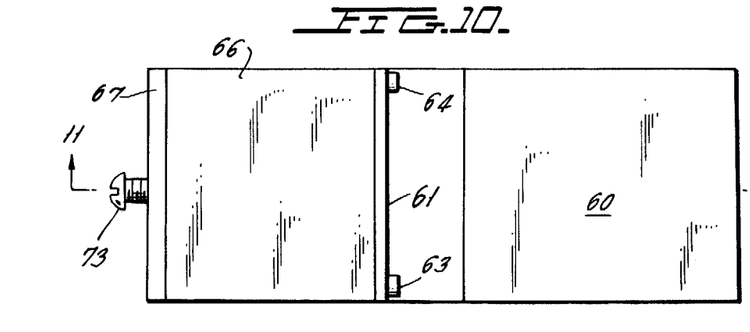
FIG. 10 is a plan view of a subassembly of wedge and damper to be used in a second embodiment of the housing of the present invention.
Figure 11:
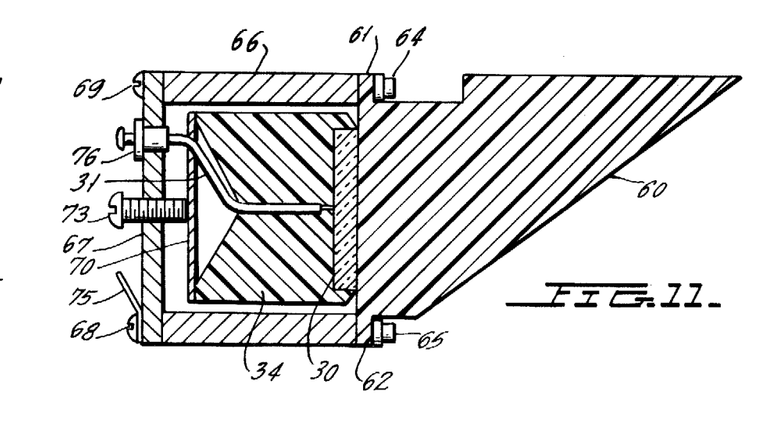
FIG. 11 is a cross-sectional view taken across the section line 11—11 in FIG. 10.
Figure 12:
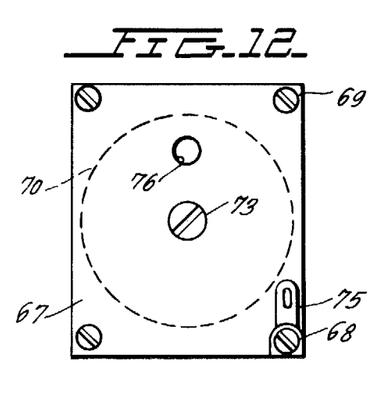
FIG. 12 is an elevation view of FIG. 11.
Figure 13:
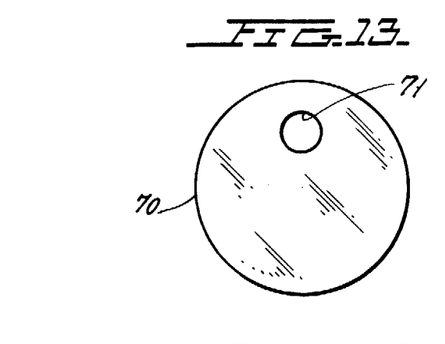
FIG. 13 is a top view of the pressure plate used in the arrangement of FIG. 11.

In manufacturing the wedge 60 of FIG. 11, it is important that the angle α be very accurately controlled and it is further important, when the transducers are used in a flowmeter according to copending application Ser. No. 6,183 (now U.S. Pat. No. 4,203,321), that the coupling material of the wedges 60 in the two opposed transducers used in a flowmeter have identical characteristics. It was found that identical pairs of transducer elements for a given system can be uniquely formed from a common billet. Moreover, when a common billet is used, the same angle is formed for both wedges by a single diagonal cut through a rectangular billet, with a subsequent finishing cut, which automatically produces the correct angles for each of the transducers and making maximum use of the material and producing as little scrap as possible. More specifically, to make the wedge 60 of FIG. 11, a billet 80 having the rectangular shape shown in FIGS. 8 and 9 is first molded of the desired Meldin polyimid amide material (or some other material, if desired). The billet 80 is rectangular in section and has dimensions corresponding to those of the ultimate wedge to be produced.

Four notches 81 to 84 are machined or otherwise formed in the rectangular billet, and end walls are defined by the notches 81 to 84. The end walls formed by notches 81 to 84 then have openings such as openings 85 and 86 formed therein which will receive the mounting screws such as screws 63, 64 and 65 in FIGS. 10 and 11 for mounting the ultimately formed wedge to the transducer crystal assembly.

The rectangular billet 80 is then saw-cut through the plane 87 in FIG. 9 and then are subsequently finished to produce two symmetric and identical wedge elements. The specific angle selected for the cut is tailored to the particular application of the transducer housing which is to receive the wedges. Thus, as was previously described, $$\sin \alpha = V_c/V_{pc},$$

where $V_c$ is the sonic velocity in the body of the billet material or of the wedge 60 in FIG. 11;

$V_{pc}$ is the sonic group velocity in the pipe wall to which the transducers are to be coupled.

Thus, each class of pipes to which the transducers are to be coupled will have their own tailored angle.

Before cutting the angle precisely, the sonic velocity of the billet is first measured and the angle is then precision-trimmed as by milling or the like so that it will have exactly the correct angle for a particular group velocity in the pipe with which the transducers are to be used. Note that a minimum of material will be lost by cutting the two wedges from a common rectangular billet 80. Also note that it is possible to trim the wedge angle to the exactly correct value by measuring the sonic velocity of the billet itself before the billet is cut.

After completing the subassembly described in connection with FIGS. 10 to 13, the subassembled transducer crystal 30, buffer 34 and coupling wedge 60 are assembled in a housing as shown in FIGS. 14 to 17. The hypotenuse 60a of right wedge 60 is flush with the bottom of the housing. This housing is formed of two U-shaped metal channels 90 and 91 which define a rectangular enclosure and which receive a top plastic plug 92. The plug 92 carries a conventional electrical connection 93 which may be identical to the connector 51 of FIG. 2 and receives the conductors 31 and 43 which are associated with the rear and front terminals, respectively, of the crystal 30.

Mounting ears 95 and 96 having captured screws 97 and 98, respectively, are suitably attached as by screws to the U-shaped brackets 90 and 91.

The interior of the rectangular housing is then filled with a suitable body of some inexpensive epoxy 99, or a polyurethane or the like. During this filling operation, the assembly including wedge 60 will be suitably held in place relative to the members 90 and 91 and after the filling operation the plastic plug 92 can be put in place. Note that plug 92 can be put in place before the filling operation and can serve as a closure for the mold defining the interior body 99. The plastic plug 92 may be fixed in position by screws such as screws 101 to 105 shown in FIGS. 16 and 17. Note that, in the embodiment of FIG. 16, the wedge 60 has been slightly foreshortened at location 100 to conform to the dimensional requirement of the particular transducer assembly.

The connector 93 can then be enclosed by a suitable connector enclosure if desired and it is now possible to mount the transducer assembly for use in a clamp-on ultrasonic measurement application or any other desired application.

Note that the assembly of FIGS. 14 to 17 will be relatively inexpensive since only a small mass of the expensive plastic coupling medium 60 is used relative to the entire volume 99 of the transducer housing.

When the transducers of the invention are used in a clamp-on flow measuring system, as described in copending application Ser. No. 6,183 (now U.S. Pat. No. 4,203,324), it is necessary to mount first and second transducers on opposing sides of a conduit with a given spacing between them. A novel mounting arrangement has been developed including a novel mounting track as shown in FIGS. 18 through 28.

Figures 18, 21, 27:
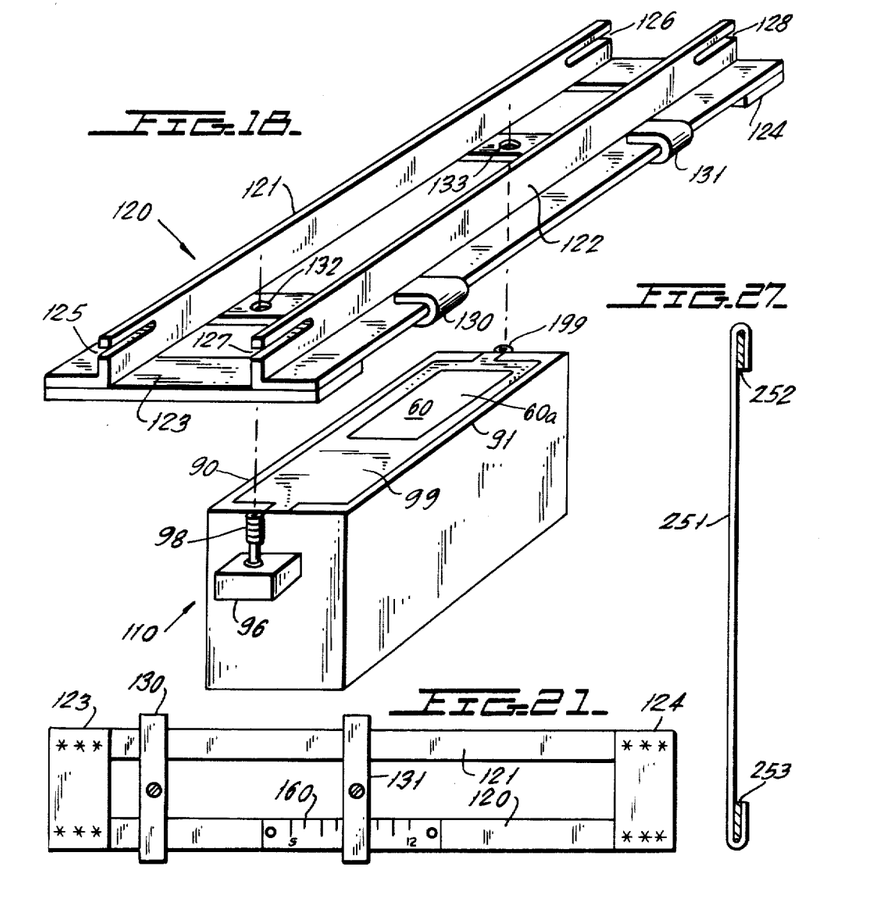
FIG. 18 is an exploded perspective view of a novel mounting track along with a transducer assembly of the type shown in FIGS. 14 to 17.
FIG. 21 is a top view of the track of FIG. 19 and particularly illustrates the novel indexing plate which can be associated with the track.
FIG. 27 is an end view of the flexible mounting sheet which is used in FIGS. 25 and 26.

The basic form of the mounting track and its connection to a transducer of the type shown in FIGS. 14 to 17 is shown in FIG. 18.

Figures 14, 15, 16, 17:
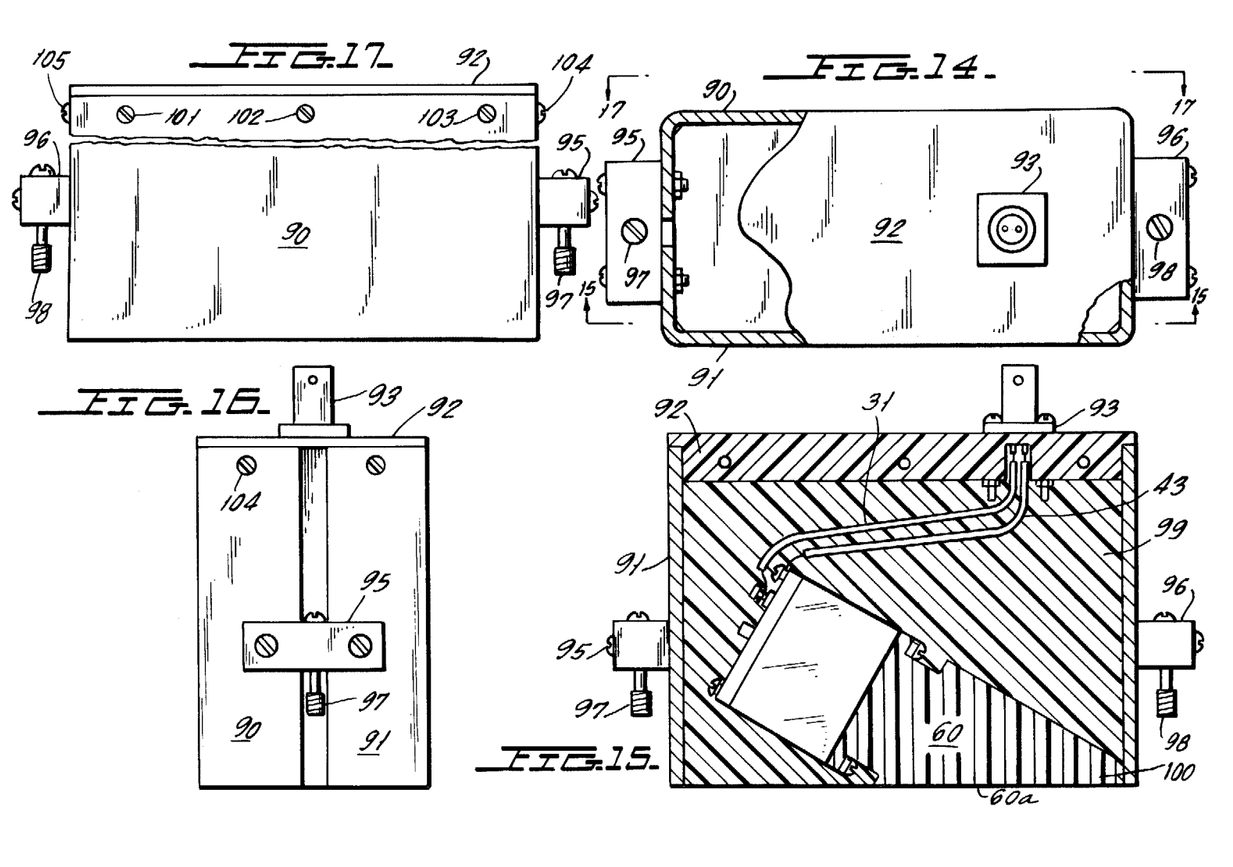
FIG. 14 is a top view of a transducer assembly using the elements of FIGS. 10 to 13.
FIG. 15 is a cross-sectional view of FIG. 14 taken across the section line 15—15 in FIG. 14.
FIG. 16 is an elevation view of FIG. 15.
FIG. 17 is a side plan view of FIG. 15.

Referring to FIG. 18, the transducer assembly 110 is of the type shown in FIG. 15, for example, and the bottom surface 60a of the transducer is shown flush with the bottom of the transducer housing. The transducer assembly 110 is connected to a novel support track assembly 120 consisting of two tracks or rails 121 and 122 which have a fixed parallel spacing from one another, as defined by spacers 123 and 124 which can be spot-welded or otherwise connected to the tracks 121 and 122. The ends of tracks 121 and 122 have strap-receiving slots 125–126 and 127–128, respectively. Slots 125 to 128 may be closed at their outer ends if it is wished to fit the straps in the slots.

Tracks 121 and 122 receive sliding clamps 130 and 131, respectively, which slide on the outwardly extending flanges of tracks 121 and 122, respectively, and contain threaded mounting openings 132 and 133, respectively. The mounting openings 132 and 133 then receive the captured mounting screws 98 and 99, respectively, of the transducer assembly 110. The location of the mounting ears 96 and 97, which receive the mounting screws 98 and 99, are so arranged that the wedge surface 60a will engage the surface of a pipe under pressure as the mounting track assemblies are fixed or clamped to the pipe. At the same time, the mounting pressure will fix the clamps 130 and 132 in a fixed position on the track.

Figures 19, 20:
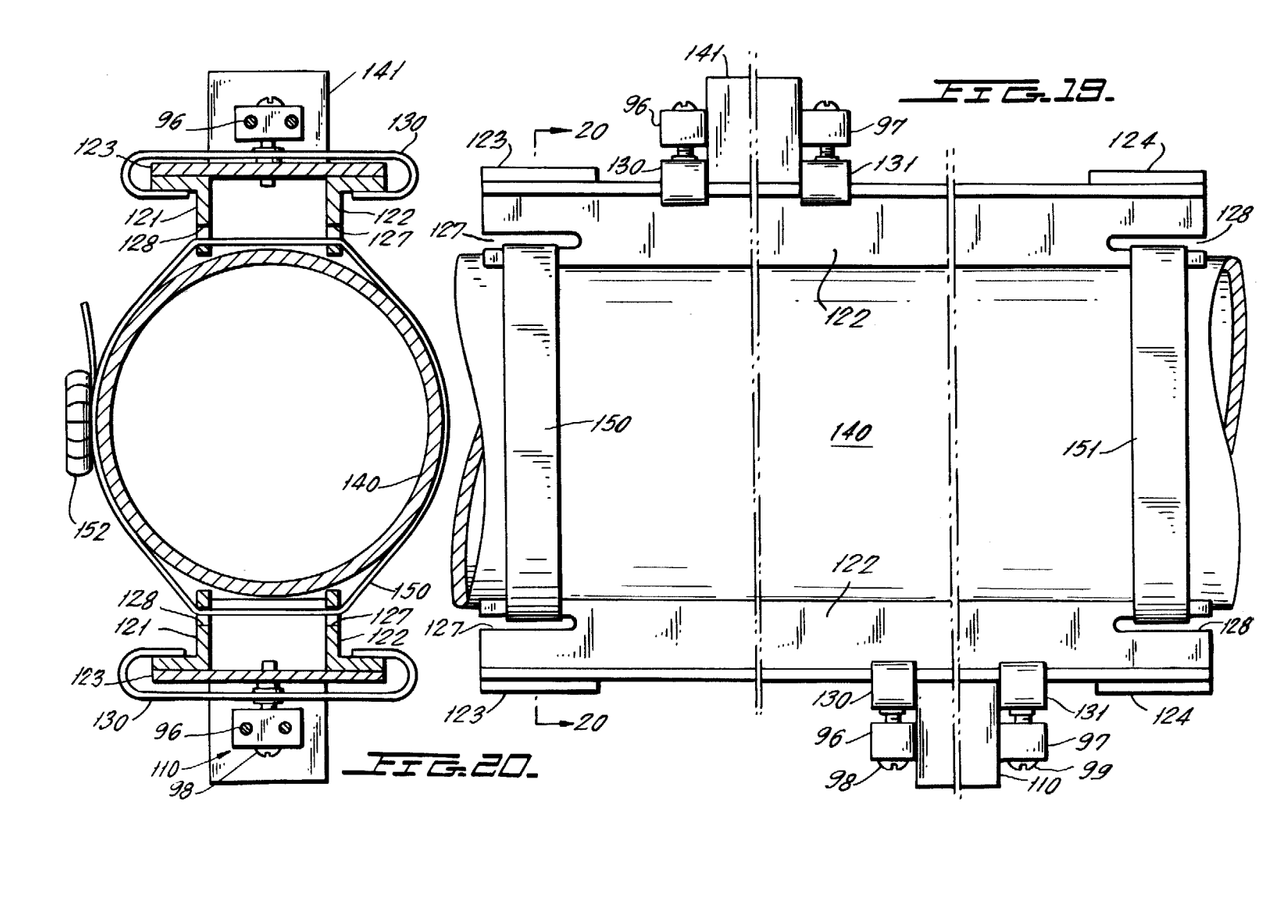
FIG. 19 is a side view of the mounting track and transducers of FIG. 18 on a pipe which carries fluid which is to be monitored by flow monitoring equipment.
FIG. 20 is a cross-sectional view of FIG. 19 taken across the section line 20—20 in FIG. 19.

FIGS. 19, 20 and 21 illustrate the mounting arrangement of FIG. 18 in connection with a pipe 140. The entire track assembly of FIG. 18 and the transducer 110 are shown on the bottom of pipe 140 in FIGS. 19 and 20. An identical assembly including the second transducer of the system, shown as transducer 141, is mounted on top of the pipe 140 by an identical track assembly, the components of which have been assigned identical numerals to those of the bottom track assembly. It is to be specifically noted that the transducers 110 and 141 are axially spaced from one another by some exact distance which has been calculated in accordance with the disclosures of U.S. Pat. No. 3,987,674 and copending application Ser. No. 6,183 (now U.S. Pat. No. 4,203,324).

In order to mount the track assemblies in place, flexible straps 150 and 151 are fitted into slots 127 and 128 of the upper and lower track assemblies and each strap is tightened by a suitable fastening buckle such as the buckle 152 of FIG. 20.

To assist in the axial location of the transducers 110 and 141, the tracks may have an index plate shown as the index plate 160 in FIG. 21. FIG. 21 is a top view of the assembly of FIG. 19 without the transducer 141 in place. The slidable clamp 131 can serve as an index marker. The index numbers on the plate 160 can then be related to an index number which is set into the adjustable circuit components of the ultrasonic flowmeter circuits. Thus, the axial spacing of the ultrasonic transducers 110 and 141 is determined, in part, by the sonic velocity of the fluid in the conduit 140. Circuit compensations can be made when different fluids are in the pipes to ensure continued high accuracy ultrasonic flow rate measurement. However, to do this, it is necessary for the ultrasonic metering circuit to have information related to the actual spacing of the transducers. By placing an index plate 160 in the system, it is now possible to place the transducers at a given index number and then make a setting in the ultrasonic circuits corresponding to this same number. The transducer circuit will then have the information related to the actual spacing between transducers and can then use this input information in carrying out various compensation actions in the measurement circuits when there is a change in the fluid sonic velocity characteristics.

The novel mounting arrangement shown in FIGS. 19 and 20 is used preferably when the width of the transducers 110 and 141 is less than about ½ the diameter of the pipe 140 and wherein the pipe diameter is not unduly large. When very large pipe diameters are used, the axial spacing between the transducers becomes relatively large and this would require relatively long track assemblies. Accordingly, where relatively large diameter pipes are used, only a single one of the track assemblies is used with each of the transducers and the mounting assembly is that shown in FIG. 22.

Figure 22:
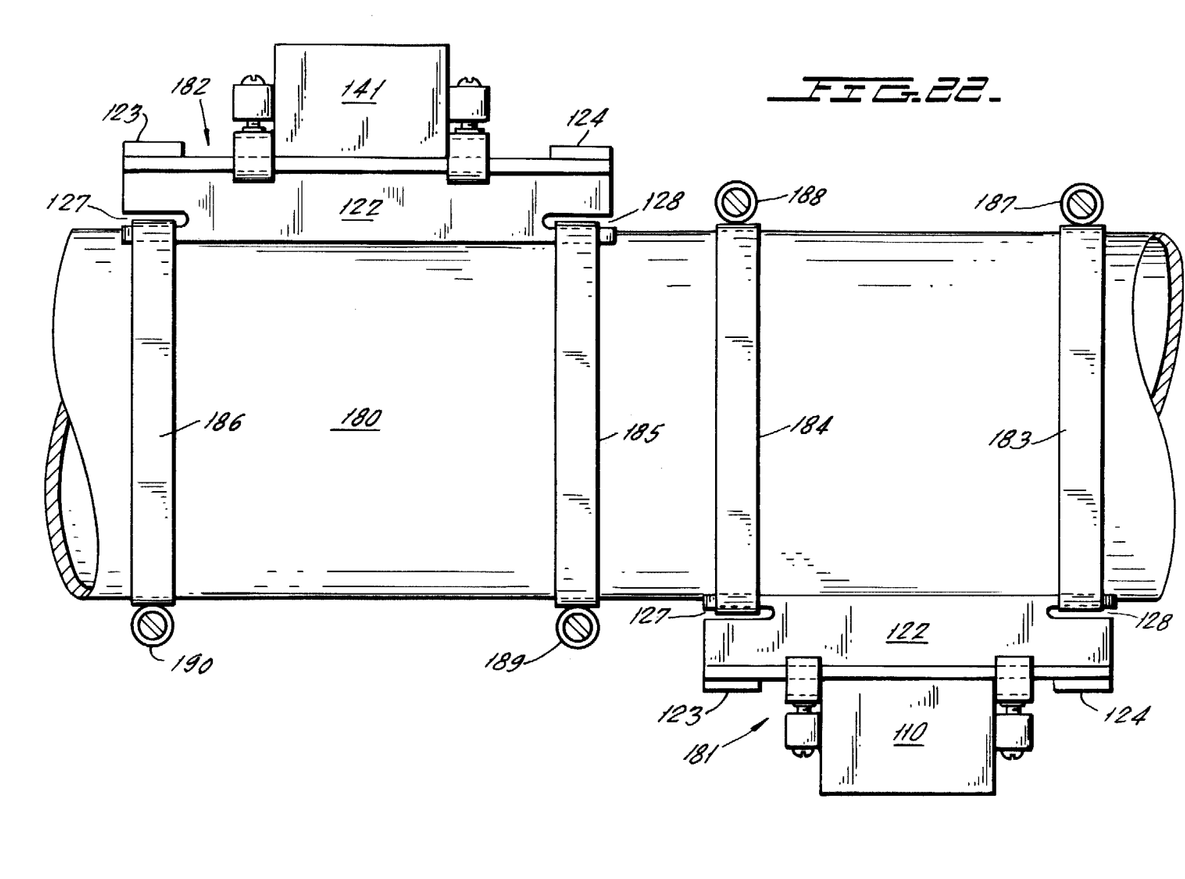
FIG. 22 is a view similar to FIG. 19 but shows a modified track arrangement for assemblies which require very wide spacing between the transducers.

Referring to FIG. 22, there is shown a relatively large diameter pipe 180 which receives the two spaced transducers 110 and 141 of FIG. 19, for example. In FIG. 22, rather than two relatively long track assemblies, each of the transducers is provided with its own respective track assembly 181 and 182, respectively, which have the same construction described in FIGS. 18 through 21 but are relatively short. Each of the track assemblies is then fixed to the pipe 180 by respective straps 183-184 and 185-186, respectively. Appropriate clamps are provided for each of the straps 183 to 186, shown as screw-operated clamps 187 to 190, respectively.

Figures 23, 24:
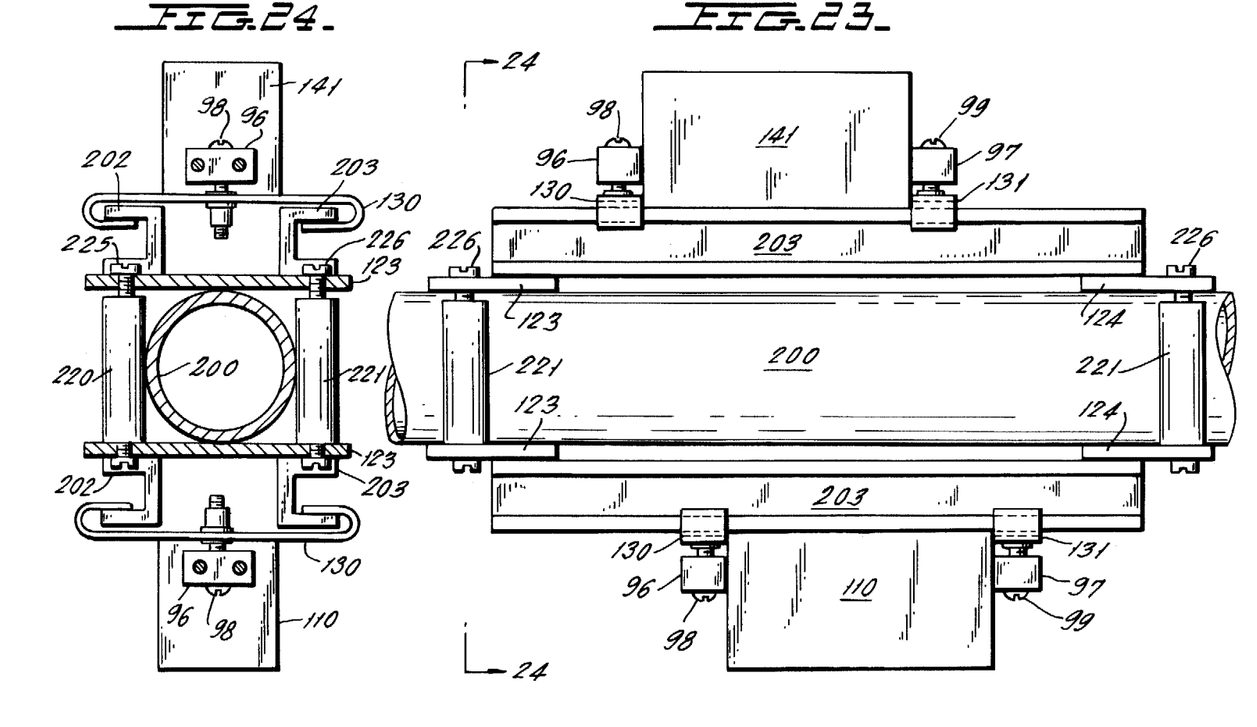
FIG. 23 is a side view of an assembly similar to that of FIG. 19 wherein the pipe diameter is relatively small and the mounting track is appropriately modified for the small diameter pipe.
FIG. 24 is a cross-sectional view of FIG. 23 taken across the section line 24—24 in FIG. 23.

A special mounting problem arises when the width of the transducers is greater than about ½ the diameter of the pipe. Thus, special mounting provisions are needed. In FIGS. 23 and 24, pipe 200 has a relatively small diameter compared to the width of the transducers 110 and 141. The mounting track assembly is slightly modified so that the angles 122 and 121 of FIG. 18 are replaced by U-shaped tracks 202 and 203, respectively. Identical upper and lower track assemblies are also used. Sliding clamps 130 and 131 are used and the spaced tracks 202 and 203 are fixed to a given spacing by the spacer bars 123 and 124. Members 123 and 124 in FIGS. 23 and 24 overlap the ends of the tracks 202 and 203. Mounting posts 221 and 220 are then clamped together by appropriate clamping screws such as clamping screws 225 and 226, respectively, in order to clamp the track assemblies to the small diameter pipe 200. The transducers are fixed to the track assemblies as previously described.

The mounting assemblies described in FIGS. 19 to 24 are particularly useful for a permanently mounted transducer assembly. It is, however, frequently desirable to have a portable unit which can be quickly connected and disconnected from a pipe.

Figure 25:
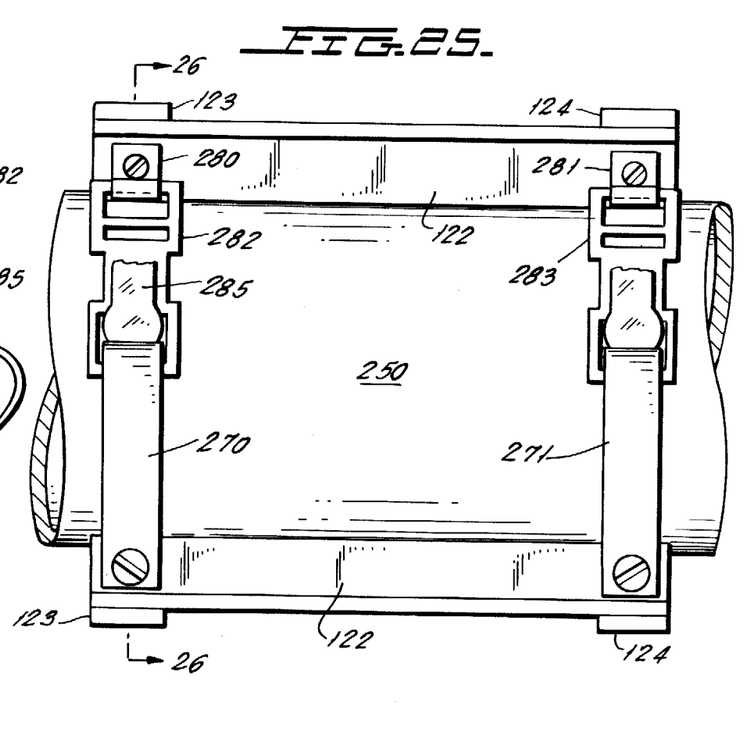
FIG. 25 is a side view of a further embodiment of a mounting arrangement for a transducer which is to be a portable member and thus the mounting arrangement permits easy connection and disconnection of the transducer to a pipe.
Figure 26:
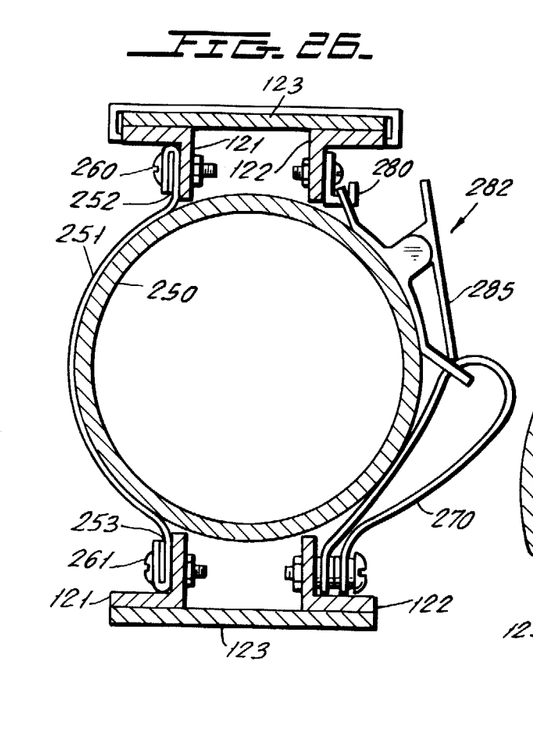
FIG. 26 is a cross-sectional view of FIG. 25 taken across the section line 26—26 in FIG. 25.
Figure 28:
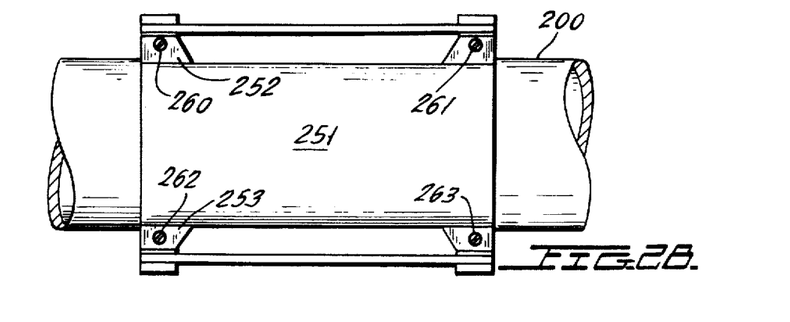
FIG. 28 is a rear view of FIG. 25 and illustrates the flexible mounting sheet of FIG. 27 clamped in place.

FIGS. 25 to 28 show a novel portable mounting arrangement which permits quick and easy connection and disconnection of the transducer mounting tracks to a pipe such as the pipe 250. In FIGS. 25, 26 and 28, the same mounting track assembly previously described is used. A flexible sheet 251, which is preferably a reinforced rubber impregnated fiber glass sheet having its upper and lower edges fixed to reinforcing strips 252 and 253, respectively, connects the two track assemblies together. While sheet 251 is flexible, it is preferably stiff in the shear mode and cannot be distorted out of a rectangular shape by reasonable shear stress. Thus, the upper and lower edges of the sheet 251 are connected to the tracks 121 of the upper and lower track assemblies as by screws 260-261 and 262-263, respectively, as best shown in FIGS. 26 and 28. Note that the length of the sheet 251 between members 252 and 253 will be cut for a specific diameter pipe and will be cut so that the track assemblies will be flat and parallel above and below the pipe when the tracks are fixed to the top and bottom of the pipe. The track assemblies are secured to one another on the other side of the pipe by flexible straps 270 and 271 shown in FIGS. 25 and 26. Straps 270 and 271 are permanently connected to the lower track 122 while the upper track 122 receives U-shaped brackets 280 and 281 (FIGS. 25 and 26) which receive one end of conventional pressure lever clips 282 and 283, respectively. Pressure lever clips 282 and 283, as shown in FIG. 26 for the clip 282, have a pressure lever 285 which is biased by an appropriate spring into engagement with the straps 270 and 271 to hold the straps in position after the strap ends have been tightened. After the straps have been threaded through the bottom end of the buckles 282 and 283 and tightened, the strap ends may be clipped onto the bottom bracket 122 as shown in FIG. 26.

It is now possible, as will be seen in FIGS. 25, 26 and 28, to easily connect and disconnect transducers which are carried in the upper and lower track assemblies above and below the pipe in FIG. 25. The novel quick-release clip, which permits quick release of the straps 270 and 271 and permits easy removal and reconnection of the transducer assemblies from the pipe 250. Moreover, the pre-cut flexible spacer sheet 251 causes automatic alignment of the spacer bars above and below the pipe 250.

Although the present invention has been described in connection with a preferred embodiment thereof, many variations and modifications will now become apparent to those skilled in the art. It is preferred, therefore, that the present invention be limited not by the specific disclosure herein, but only by the appended claims.

What is claimed is:

1. A transducer structure comprising, in combination:
a transducer crystal having electrodes which are energizable to produce mechanical energy; a sonic coupling body having a sonic output surface coupled to one surface of said crystal and conducting sonic energy from said one surface of said crystal to its said sonic output surface; said sonic coupling body comprised of a plastic material having sonic-temperature characteristics which are sufficiently close to those of steel to enable coupling to a steel pipe for good operation over a wide temperature range; said sonic coupling body having the shape of a rectangular wedge; the base of said wedge coupled to said one surface of said crystal; one side of said wedge defining said sonic output surface.

2. The structure of claim 1, wherein said sonic coupling body is made of a polyimid amide.

3. The structure of claim 2, wherein said sonic coupling body is formed by the process of compression molding.

4. The transducer structure of claim 1, wherein said transducer is adapted to be coupled to a pipe having a group velocity $V_{ps}$; the sonic velocity of said sonic coupling body being $V_s$; the angle between said one surface of said crystal and said sonic output surface being $\alpha$; said angle $\alpha$ being such that $$\sin \alpha = V_c/V_{ps}.$$

5. A transducer structure comprising a transducer crystal having electrodes which are energizable to produce mechanical energy; a sonic coupling body having a sonic output surface coupled to one surface of said crystal and conducting sonic energy from said one surface of said crystal to its said sonic output surface; said sonic coupling body having the shape of a right rectangular wedge; the base of said wedge coupled to said one surface of said crystal; the hypotenuse of said wedge defining said sonic output surface; said transducer structure being adapted to be coupled to a metallic pipe having a group velocity $V_{ps}$; the sonic velocity of said sonic coupling body being $V_c$; the angle between said one surface of said crystal and said sonic output surface being $\alpha$; said angle $\alpha$ being such that $$\sin \alpha = V_c/V_{ps}.$$

6. The structure of claim 5, wherein said sonic coupling body is made of a polyimid amide.

7. A transducer structure comprising, in combination: a transducer crystal having electrodes which are energizable to produce mechanical energy; a sonic coupling body having a sonic output surface coupled to one surface of said crystal and conducting sonic energy from said one surface of said crystal to its said sonic output surface; and a damper connected to the second surface of said crystal; said second surface being opposite said one surface; said damper comprising a plastic body having a metal powder and an elastomeric sonic absorptive filler distributed therethrough; said damper having a rear surface; said rear surface having a generally conical depression thereon; said sonic coupling body having the shape of a right rectangular wedge; the base of said wedge coupled to said one surface of said crystal; the hypotenuse of said wedge defining said sonic output surface.

8. The transducer structure of claim 7, wherein said elastomeric filler consists of particles of a polysulphone.

9. The transducer structure of claim 7 or 8, wherein said sonic coupling body is made of a polyimid amide.

* * * * *